US00PP32914P2

(12) United States Plant Patent
Palmer et al.

(10) Patent No.: US PP32,914 P2
(45) Date of Patent: Mar. 23, 2021

(54) ***HYPOESTES* PLANT NAMED 'G14158'**

(50) Latin Name: *Hypoestes phyllostachya*
Varietal Denomination: G14158

(71) Applicants: Irene E. Palmer, Arden, NC (US); Michael S. Uchneat, Bellefonte, PA (US)

(72) Inventors: Irene E. Palmer, Arden, NC (US); Michael S. Uchneat, Bellefonte, PA (US)

(73) Assignee: GARDENGENETICS LLC, Bellefonte, PA (US)

( * ) Notice: Subject to any disclaimer, the term of this patent is extended or adjusted under 35 U.S.C. 154(b) by 0 days.

(21) Appl. No.: 16/873,549

(22) Filed: Apr. 30, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. Anne Whealy

(57) ABSTRACT

A new and distinct cultivar of *Hypoestes* plant named 'G14158', characterized by its upright and mounding plant habit; moderately vigorous growth habit; freely branching habit; large dark green and red purple bi-colored leaves; and relative tolerance to high light conditions.

1 Drawing Sheet

Botanical designation: *Hypoestes phyllostachya*.
Cultivar denomination: 'G14158'.

BACKGROUND OF THE INVENTION

The present invention relates to a new and distinct cultivar of *Hypoestes* plant, botanically known as *Hypoestes phyllostachya* and hereinafter referred to by the name 'G14158'.

The new *Hypoestes* plant is a product of a planned breeding program conducted by the Inventors in Bellefonte, Pa. The objective of the breeding program is to create new vigorous *Hypoestes* plants with attractive leaves and high light tolerance.

The new *Hypoestes* plant is a naturally-occurring branch mutation of an unnamed proprietary selection of *Hypoestes phyllostachya*, not patented. The new *Hypoestes* plant was discovered and selected by the Inventors on a single plant within a population of plants of the mutation selection in a controlled greenhouse environment in Bellefonte, Pa. on Aug. 15, 2014.

Asexual reproduction of the new *Hypoestes* plant by terminal cuttings in a controlled greenhouse environment in Bellefonte, Pa. since Aug. 15, 2014 has shown that the unique features of this new *Hypoestes* plant are stable and reproduced true to type in successive generations.

SUMMARY OF THE INVENTION

Plants of the new *Hypoestes* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G14158'.

These characteristics in combination distinguish 'G14158' as a new and distinct *Hypoestes* plant:

1. Upright and mounding plant habit.
2. Moderately vigorous growth habit.
3. Freely branching habit.
4. Large dark green and red purple bi-colored leaves.
5. Relatively tolerant to high light conditions.

Compared to plants of the mutation parent selection, plants of the new *Hypoestes* differ primarily in the following characteristics:

1. Plants of the new *Hypoestes* are more vigorous than and not as compact as plants of the mutation parent selection.
2. Plants of the new *Hypoestes* have thicker leaves than plants of the mutation parent selection.
3. Plants of the new *Hypoestes* are more tolerant to high light conditions than plants of the mutation parent selection.

Compared to plants of *Hypoestes phyllostachya* 'G14160', disclosed in U.S. Plant Pat. No. 29,842, plants of the new *Hypoestes* differ primarily in the following characteristics:

1. Plants of the new *Hypoestes* are not as vigorous as plants of 'G14160'.
2. Plants of the new *Hypoestes* are more freely branching than plants of 'G14160'.
3. Plants of the new *Hypoestes* and 'G14160' differ in leaf color as plants of the new *Hypoestes* have brighter red purple-colored splotches than plants of 'G14160'.

Plants of the new *Hypoestes* can also be compared to plants of *Hypoestes phyllostachya* 'Splash Select Red', not patented. In side-by-side comparisons, plants of the new *Hypoestes* differ primarily from plants of 'Splash Select Red' in the following characteristics:

1. Plants of the new *Hypoestes* are more vigorous than and not as compact as plants of 'Splash Select Red'.

2. Plants of the new *Hypoestes* have thicker leaves than plants of 'Splash Select Red'.
3. Plants of the new *Hypoestes* are more tolerant to high light conditions than plants of 'Splash Select Red'.

BRIEF DESCRIPTION OF THE PHOTOGRAPH

The accompanying photograph illustrates the overall appearance of the new *Hypoestes* plant showing the colors as true as it is reasonably possible to obtain in colored reproductions of this type. Colors in the photograph may differ slightly from the color values cited in the detailed botanical description which accurately describe the colors of the new *Hypoestes* plant.

The photograph (FIG. 1) is a side perspective view of a typical plant of 'G14158' grown in a container.

DETAILED BOTANICAL DESCRIPTION

The aforementioned photograph and following observations and measurements describe plants grown during the late winter in 10.8-cm containers in a corrugated polycarbonate-covered greenhouse in Carleton, Mich. and under cultural practices typical of commercial potted *Hypoestes* production. During the production of the plants, day temperatures averaged 20° C., night temperatures averaged 18° C. and light levels averaged 6,790 foot-candles. Plants were pinched one time and were nine weeks old when the photographs and description were taken. In the following description, color references are made to The Royal Horticultural Society Colour Chart, 2015 Edition, except where general terms of ordinary dictionary significance are used.

Botanical classification: *Hypoestes phyllostachya* 'G14158'.

Parentage: Naturally-occurring branch mutation of an unnamed proprietary selection of *Hypoestes phyllostachya*, not patented.

Propagation:

Type: By terminal cuttings.

*Time to initiate roots, summer*.—About 7 to 10 days at ambient temperatures about 18° C. and soil temperatures about 22°.

*Time to initiate roots, winter*.—About 10 to 14 days at ambient temperatures about 18° C. and soil temperatures about 22° C.

*Time to produce a rooted plant, summer*.—About three to four weeks at ambient temperatures about 18° C. and soil temperatures about 22° C.

*Time to produce a rooted plant, winter*.—About four to five weeks at ambient temperatures about 18° C. and soil temperatures about 22° C.

*Root description*.—Medium in thickness, fibrous; close to white to creamy white in color, actual color of the roots is dependent on substrate composition, water quality, fertilizers, substrate temperature and age of roots.

*Rooting habit*.—Moderately freely branching; medium density.

Plant description:

*Plant and growth habit*.—Upright and mounded plant form; freely branching habit with lateral branches potentially forming at every node; moderately vigorous growth habit and moderate growth rate.

*Plant height*.—About 17 cm.

*Plant diameter or spread*.—About 18 cm.

*Lateral branches*.—Length: About 14 cm. Diameter: About 4 mm to 5 mm. Internode length: About 2.5 cm to 3 cm. Strength: Strong, sturdy. Aspect: Primary branches are mostly upright; secondary lateral branches are about 30° to 45° from vertical. Texture and luster: Sparsely pubescent; somewhat glossy. Color: Developing: Close to between 144A and 146A. Developed: Close to 187A.

Leaf description:

*Arrangement*.—Opposite; simple.

*Length, largest leaves*.—About 9.75 cm.

*Width, largest leaves*.—About 7.5 cm.

*Shape*.—Broadly ovate.

*Apex*.—Acute to broadly acute.

*Base*.—Obtuse with truncate tendencies.

*Margin*.—Sinuate; moderately undulate.

*Venation pattern*.—Pinnate, arcuate.

*Texture and luster, upper surface*.—Rugose, glabrous; somewhat glossy.

*Texture and luster, lower surface*.—Rugose, glabrous; slightly glossy.

*Color*.—Developing leaves, upper surface: Ground color, close to NN137A; interveinal splotches, close to 60A. Developing leaves, lower surface: Ground color, close to 147A; interveinal splotches, close to 186D. Fully expanded leaves, upper surface: Ground color, close to between 147A and NN137A; interveinal splotches, close to 60A; midvein proximally, close to N186A and distally, close to 147A; lateral venation, close to 147A. Fully expanded leaves, lower surface: Ground color, close to 147A variably tinged with close to 187A; interveinal splotches, close to 186D; venation proximally, close to 187A and distally, close to 147A.

*Petioles*.—Length: About 3.5 cm to 4 cm. Diameter: About 2 mm by 3 mm. Strength: Moderately strong, flexible. Texture and luster, upper and lower surfaces: Sparsely pubescent; moderately glossy. Color, upper surface: Close to N186A. Color, lower surface: Close to 187A.

Flower description: To date, flower initiation and development have not been observed on plants of the new *Hypoestes*.

Pathogen & pest resistance: Plants of the new *Hypoestes* have been observed to have moderate tolerance to *Xanthomonas campestris*. To date, plants of the new *Hypoestes* have not been observed to be resistant to pests and other pathogens common to *Hypoestes* plants.

Temperature tolerance: Plants of the new *Hypoestes* have been observed to tolerate low temperatures about 4° C. and to be suitable for USDA Hardiness Zones 10 and 11.

It is claimed:

1. A new and distinct *Hypoestes* plant named 'G14158' as illustrated and described.

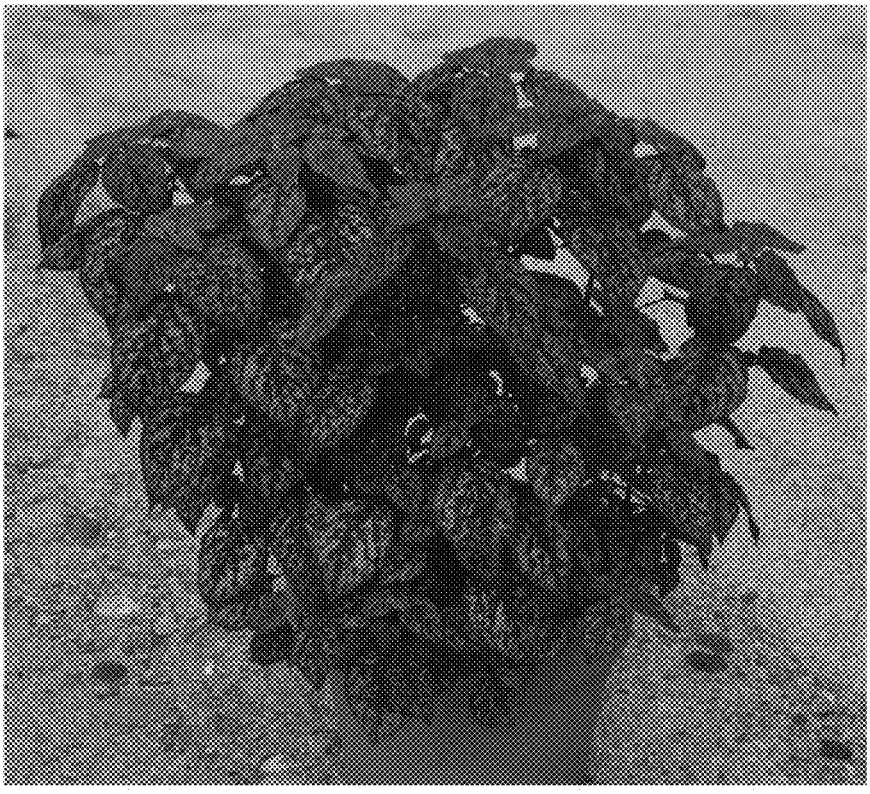

* * * * *